United States Patent [19]

Tao

[11] Patent Number: 4,698,314
[45] Date of Patent: Oct. 6, 1987

[54] METHOD FOR MEASUREMENT OF GAS CONCENTRATION

[75] Inventor: Hiroaki Tao, Ibaraki, Japan

[73] Assignees: Agency of Industrial Science & Technology; Ministry of International Trade & Industry, both of Tokyo, Japan

[21] Appl. No.: 797,864

[22] Filed: Nov. 14, 1985

[30] Foreign Application Priority Data

Nov. 14, 1984 [JP] Japan .................................. 59-240300

[51] Int. Cl.$^4$ ...................... G01N 21/47; G01N 33/20
[52] U.S. Cl. ...................................... 436/171; 436/75; 436/76; 436/77; 436/103; 436/104; 436/181; 250/423 P
[58] Field of Search .............. 422/89, 91, 186, 186.03; 436/35, 52, 103, 104, 181, 75–77; 250/214 A, 215, 574, 576, 423 R, 492.1, 504 R, 423 P

[56] References Cited

U.S. PATENT DOCUMENTS

| 3,869,362 | 3/1975 | Machi et al. ........................ 55/6 X |
| 4,134,344 | 2/1982 | Johns et al. .................. 422/186.3 X |
| 4,199,419 | 4/1980 | Holroyd et al. ............. 422/186.3 X |
| 4,233,030 | 11/1980 | Twitchett et al. ............... 422/186 X |
| 4,447,543 | 5/1984 | Harada et al. .................... 422/91 X |

Primary Examiner—Barry S. Richman
Assistant Examiner—Jill Johnston
Attorney, Agent, or Firm—Oblon, Fisher, Spivak, McClelland & Maier

[57] ABSTRACT

A gas concentration measuring method comprises irradiating a sample gas with ultraviolet light in the presence of oxygen, thereby converting a specific gas for detection contained in the sample gas into fine oxide particles by photochemical reaction, irradiating the sample gas having the fine oxide particles contained therein with light, and detecting scattered light emitted from the fine oxide particles contained in the sample gas.

2 Claims, 8 Drawing Figures

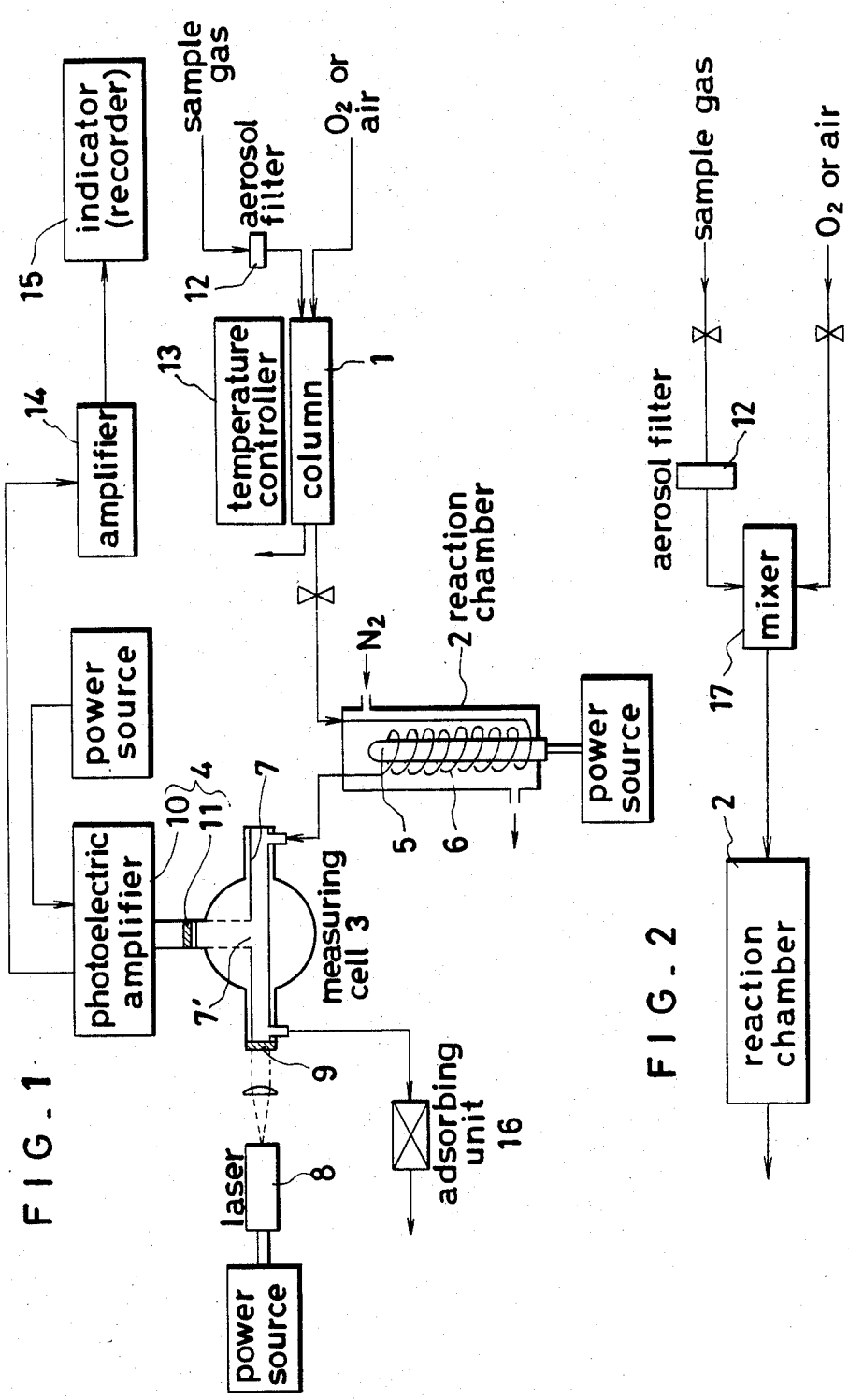

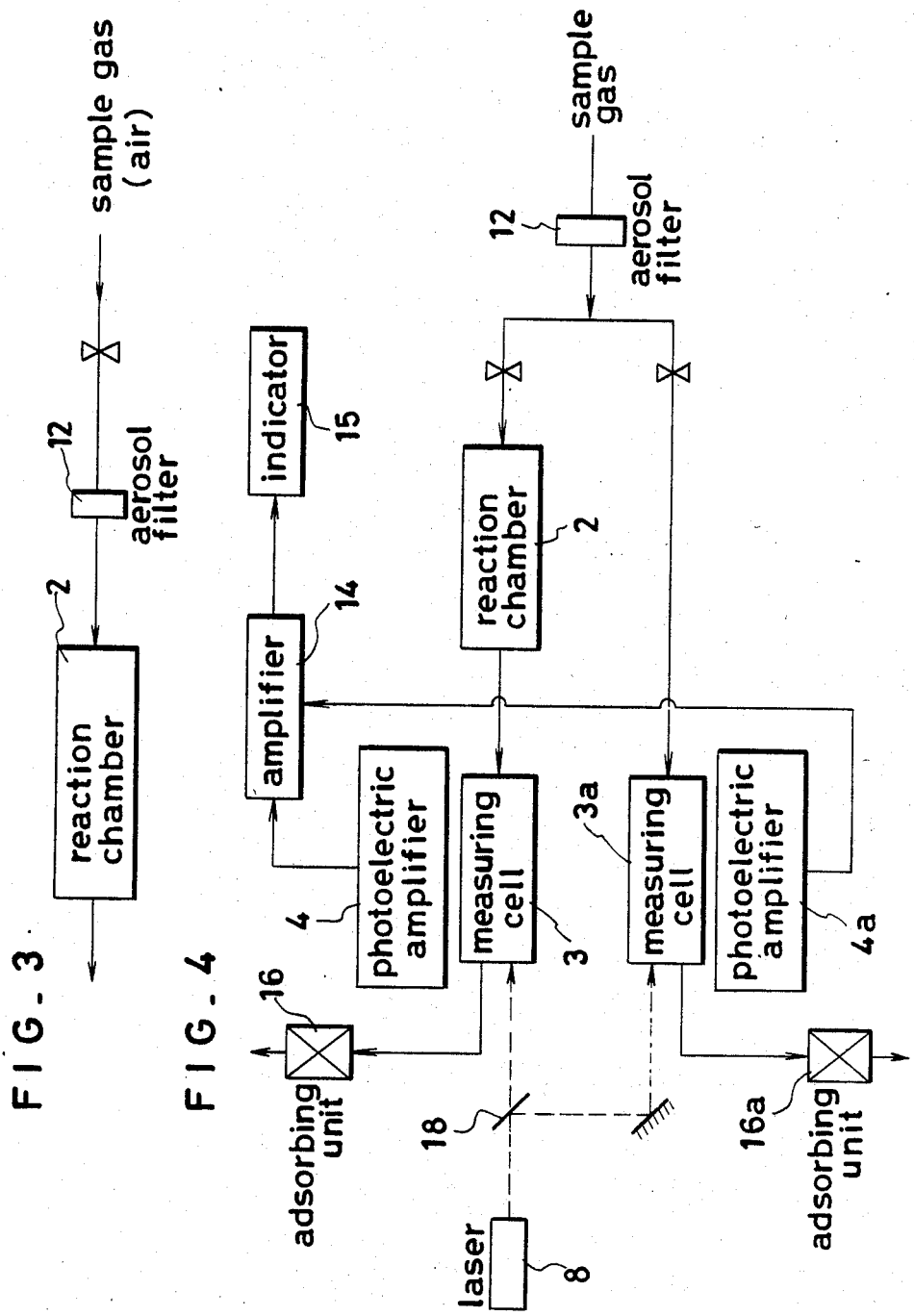

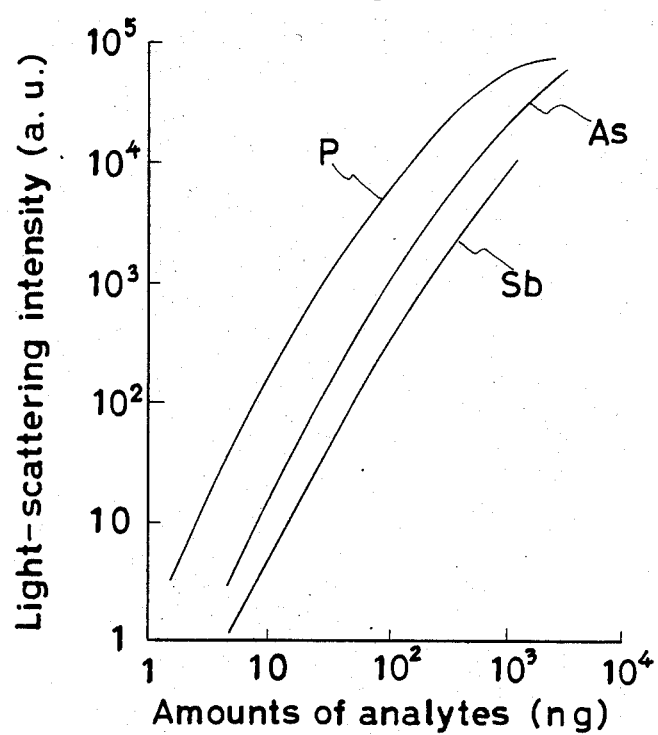
FIG_5
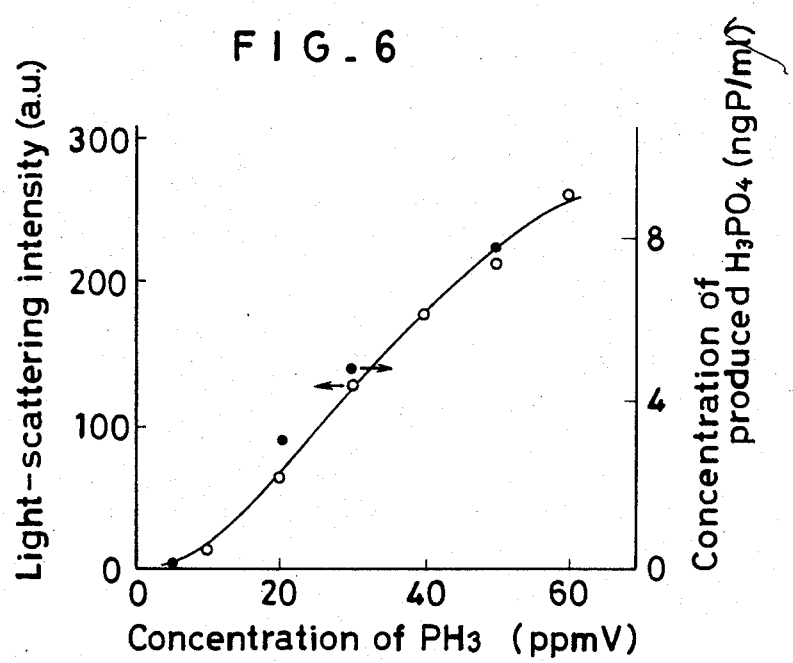
FIG_6

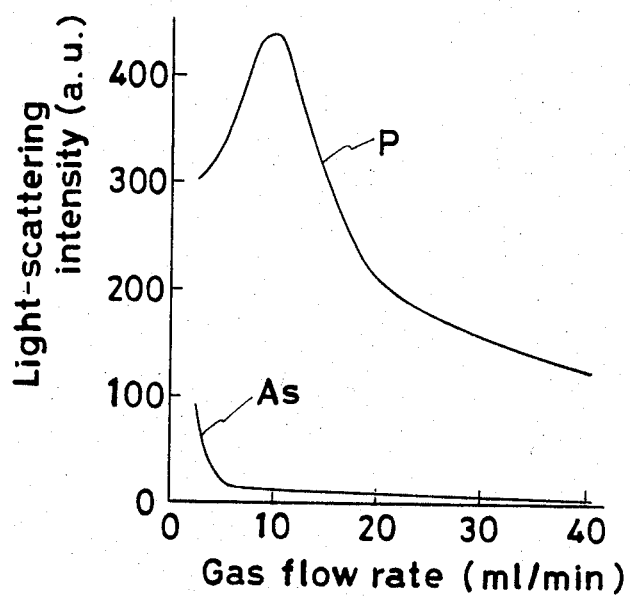
FIG_7
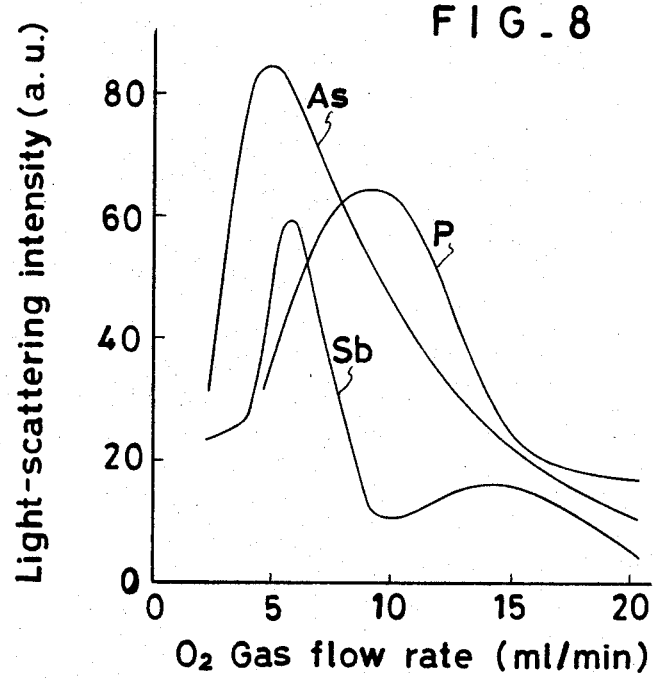
FIG_8

METHOD FOR MEASUREMENT OF GAS CONCENTRATION

FIELD OF THE INVENTION AND RELATED ART STATEMENT

This invention relates to method and apparatus for the measurement of a specific gas contained in a minute amount in a body of gas.

Solar cells, optical devices, super-high speed integrated circuits, etc. are now commonly produced using compound semiconductors. Manufacture of these compound semiconductors necessitates use of such poisonous gases as arsine ($AsH_3$) and phosphine ($PH_3$). Detection of possible inclusion of such a poisonous gas in the gas discharged from the system used for the manufacture of a compound semiconductor is extremely important for the preservation of a safe working environment.

As means for detecting a gas contained in a minute amount (on the ppm order or less) in a given body of gas such as air, (i) the flame photometric method using hydrogen-nitrogen flame, (ii) the photo-ionization method which comprises ionizing a sample gas by irradiation with ultraviolet light and determining the gas concentration based on the ion current generated in consequence of the ionization, (iii) the chemiluminescence spectrometric method which utilizes the reaction of the gas with ozone, (iv) the infrared spectrophotometric method which examines the absorption of infrared ray by the gas, (v) the chemical reaction-atomic absorption spectrometric method which comprises causing the gas to react with mercury oxide and indirectly determining the gas concentration based on the mercury vapor generated in consequence of the reaction, (vi) the optical reading method with a test tape which determines the gas concentration based on the decrease in the amount of light transmitted through a test tape impregnated with a reagent capable of developing a color on exposure to the gas, and (vii) the electrochemical method (diaphragm galvanic battery type and fixed potential electrolytic type) which utilizes the oxidative reaction of the gas on the surface of an electrode have been known to the art.

Various gas detectors have been proposed based on the methods described above. Each of these conventional gas detectors has its own demerits. The gas detectors employing methods iv, vi, and vii are deficient in sensitivity. Those employing ii, v, vi, and vii suffer from inferior gas selectivity. The gas detector employing method i inevitably entails the possibility of zero drift because it relies on the flame, generally an instable factor, and it has the possibility of causing explosion because it utilizes hydrogen flame. The detector employing method iii relies on the operation of a vacuum pump and an ozone generator and necessitates maintenance of these devices, and the detector employing method v is required to tolerate use of highly poisonous mercury oxide. Therefore, these detectors require further improvement before they can be used as effective automatic analyzers.

OBJECT AND SUMMARY OF THE INVENTION

An object of this invention is to provide method and apparatus for the measurement of gas concentration, which has high sensitivity and high selectivity.

Another object of this invention is to provide a gas concentration measuring apparatus which has a simple and compact structure, permits easy operation and maintenance, enjoys high operational reliability, and suits adoption as an automatic analyzer.

To attain the objects described above, this invention provides an apparatus which operates on a method comprising the steps of irradiating a sample gas with ultraviolet light in the presence of oxygen gas thereby converting the specific gas of interest contained in the sample gas into fine oxide particles, irradiating the sample gas now containing the fine oxide particles with light, and measuring the scattered light consequently emitted from the fine oxide particles.

This invention effects the determination of the concentration of the specific gas for detection, as described above, by converting the gas contained in the given sample gas into fine oxide particles by means of ultraviolet light, then irradiating the sample gas containing the fine oxide particles with light, and measuring the scattered light emitted from the fine oxide particles. Unlike the conventional methods which rely on use of dangerous flames and reagents, the apparatus of the present invention permits the measurement to be carried out easily and accurately and even enables a sample of the atmospheric air to be analyzed directly.

The other objects and characteristics of the present invention will become apparent from the further description given below with reference to the accompanying drawings.

BRIEF DESCRIPTION OF THE DRAWINGS

FIG. 1 is a block diagram of a gas concentration measuring apparatus as the first embodiment of this invention.

FIG. 2 is a block diagram illustrating another version of the sample inlet part of the gas concentration measuring apparatus of FIG. 1.

FIG. 3 is a block diagram illustrating yet another version of the sample inlet part.

FIG. 4 is a block diagram illustrating a gas concentration measuring apparatus as the second embodiment of this invention.

FIG. 5 is a graph showing calibration curves of phosphine, arsine and stibine.

FIG. 6 is a graph showing the relation among the concentration of sample gases, the light-scattering intensity and the concentration of produced oxide particles.

FIG. 7 is a graph showing the relation between the flow rate of sample gases and the light-scattering intensity in one Example.

FIG. 8 is a graph showing the relation between the flow rate of sample gases and the light-scattering intensity in another Example.

DESCRIPTION OF PREFERRED EMBODIMENTS

FIG. 1 represents one embodiment of the gas concentration measuring apparatus of the present invention. As illustrated, the gas concentration measuring apparatus essentially comprises a column 1 for concentrating and separating a gas to be measured, a photochemical reaction chamber 2 for irradiating a mixed gas of the gas and oxygen with ultraviolet light thereby converting the gas into optically measurable fine oxide particles, a measuring cell 3 for irradiating the optically measurable fine oxide particles with light, and a detection part 4 for efficiently detecting the light emitted from the fine oxide particles.

At the center of the photochemical reaction chamber 2 is positioned an ultraviolet lamp 5 such as a mercury lamp, a xenon lamp, or a $D_2$ lamp, and a quartz tube 6 is helically wound around the lamp 5 so as to irradiate the gas passing through the interior of the chamber amply with the ultraviolet light. One end of the quartz tube 6 is connected to the concentrating and separating column 1 through the medium of a gas flow rate controller and the other end of the quartz tube is connected to the measuring cell 3. To ensure effective irradiation of the sample gas with the ultraviolet light, the photochemical reaction chamber 2 is desired to be formed of a material such as aluminum which excels in reflectance of light or to have the inner surface thereof lined or plated with a substance excelling in reflectance of light. Inside the measuring cell 3 is disposed a pipe 7 for passing the sample gas. The inner wall surface of this pipe 7 is coated with delustering black paint for curbing possible background scattering. The pipe 7 is closed at one end thereof with an optical filter 9 and at the other end thereof with quartz glass and is provided at the portion thereof opposed to the detecting part 4 with a glass window 7'. A light source for irradiating the sample gas led to the pipe 7 with the light consists of a laser or lamp 8 and an optical filter 9. In this embodiment, the light is led into the pipe 7 through the optical filter 9 and is therefore caused to flow counter to the sample gas introduced through the other end of the pipe 7.

The wavelength of the irradiating light emitted by the light source is not specifically limited. Since the sensitivity of a photoelectric amplifier 10 used in the detecting part 4 falls mainly in the wavelength range of 200 to 900 nm, any light source having a radiation in this range can be used. The detecting part 4 consists of the photoelectric amplifier 10 and an optical filter 11. The present system which makes use of the photochemical reaction of oxygen and the sample gas becomes most sensitive when the irradiating light and the detecting light have an identical wavelength. It is, therefore, desirable that the optical filter 11 of the detecting part 4 should be of the same kind as the optical filter 9 which is used in the light source.

The gas component subjected to the measurement by this invention is a gas which by nature undergoes, an exposure to the ultraviolet light, dissociation with generation of a radical capable of forming oxide molecules through a chain reaction with oxygen. Examples of gases answering this description are elementary gases and compound gases such as arsine, phosphine, stibine, germane, and hydrogen selenide which are used for the manufacture of semiconductors. This invention is not limited to the gases cited above but may be effectively used for the measurement of the concentration of hydrogen sulfide gas, for example.

In the gas concentration measuring apparatus constructed as described above, a sample gas discharged from a system for the manufacture of semiconductors, for example, is first passed through an aerosol filter 12 to be deprived of foreign particles such as dust and then led into the concentrating and separating column 1 incorporating therein a gas chromatographic unit to effect selective adsorption and separation of the gas being detected. The gas which has been adsorbed on the gas chromatographic unit is eluted by elevating the temperature of the column 1 to a prescribed level by a temperature controller 13. The eluted gas is forwarded to the quartz tube 6 of the photochemical reaction chamber 2 by using a carrier gas. The concentrating and separating column is used when the concentration of the gas subjected to detection is less than the ppm order or when the gas is a mixture of a plurality of gases. When the gas for detection contained in the sample gas is of a single component and the concentration of the gas in the sample gas is relatively high (on the ppm order, for example), the sample gas which has been treated by the aerosol filter 12 is led, without being concentrated and separated, to a mixer 17 as illustrated in FIG. 2. In the mixer 17, the sample gas is mixed with a prescribed amount of oxygen and then forwarded to the photochemical reaction chamber 2. When the sample gas contains oxygen amply as in the case of atmospheric air, it may be deprived of dust by the aerosol filter 12 and immediately forwarded to the photochemical reaction chamber 2 as illustrated in FIG. 3. As the carrier gas, oxygen gas, argon gas, or helium gas may be used.

If oxygen intervenes between the helical quartz tube 6 and the ultraviolet lamp 5 inside the reaction chamber 2, it absorbs the ultraviolet light and impairs the efficiency of the reaction. To avoid this trouble, an inert gas such as nitrogen gas is passed through the interior of the reaction chamber 2 to expel the oxygen out of the reaction chamber. The inert gas so passed concurrently serves to cool the lamp.

By virtue of the helical quartz tube 6, the sample gas and the oxygen gas are caused to flow about the external boundary of the ultraviolet lamp 5. When the mixed gas is exposed to the ultraviolet light, the gas under detection contained in the sample gas is dissociated with generation of a radical. Then, the radical so formed produces oxide molecules through a chain reaction with oxygen. The oxide molecules grow into seeds through repeated collision and association and the seeds conglomerate into fine oxide particles of sizes in the range of about 0.1 to 1.0 $\mu$m. In the case of phosphine, for example, the gas is finally converted into phosphoric acid ($H_3PO_4$) mist consisting of particles 0.3 to 0.5 $\mu$m in diameter.

Qualitatively, this photochemical reaction proceeds so that the conversion of the gas into fine oxide particles heightens in proportion as the amount of the ultraviolet light used for the irradiation increases and the amount of oxygen present in the sample gas increases. As regards the reaction temperature, the conversion is not particularly affected by the temperature, which ranges from room temperature to the neighborhood of 60° 1 C.

In the case of phosphine gas as an object of detection, for example, when a sample gas containing phosphine in a concentration of 50 ppm and oxygen in a concentration of 50% is led at a flow volume of 20 ml/min into a quartz tube about 600 mm in overall length helically wound around a 4.9-W mercury lamp and irradiated with the ultraviolet light, the phosphine in the sample gas is completely oxidized and 10 to 20% of the oxidized phosphine is converted into fine oxide particles. The sample gas which now contains the fine oxide particles of the gas for detection is forwarded to the measuring cell 3. When the sample gas in the pipe 7 of the cell 3 is irradiated with the light from the lamp 8, the light is scattered by the fine oxide particles. The phenomenon of light scattering thus caused gains in intensity in proportion to the amount of the fine oxide particles contained in the sample gas. The scattered light is passed through the glass window 7' and received by the photoelectric amplifier 10 and consequently converted into an electric signal. The electric signal is amplified by the amplifier 14 and then forwarded to an indicator or recorder 15. The determination of the gas concentration is attained by preparatorily passing a standard gas through the apparatus thereby finding the relation between the gas concentration and the intensity of scattered light, drawing a calibration curve by plotting the data so found, then passing a given sample gas through the same apparatus thereby measuring the intensity of scattered light, and calculating the gas concentration by applying the found intensity of scattered light to the calibration curve. The graph of FIG. 5 represents one example of calibration curves obtained by feeding phosphine (P), arsine (As), and stibine (Sb) with the respectively optimum oxygen flow rates to the apparatus of FIG. 1 and analyzing the effluent gases. The inclinations of these calibration curves do not reach "1" particularly at low concentrations possibly because in the region of low concentrations, the speed of conglomeration is too low for smooth growth of fine oxide particles.

The spent sample gas discharged from the measuring cell 3 is passed through an adsorbing unit 16 to be deprived of the fine oxide particles by adsorption, so that the gas finally released into the ambient air will not cause any air pollution.

When the sample gas contains a substance causing scattered light, fluorescence, or phosphorescence, for example, the sample gas which has been treated by the aerosol filter 12 is divided into two parts and one part of the sample is led into the photochemical reaction chamber 2 and irradiated with the ultraviolet light to effect conversion of the specific gas for detection into fine oxide particles and the sample gas now containing the fine oxide particles is led to the measuring cell 3 as illustrated in FIG. 4. The remaining part of the sample gas, in the meantime, is led directly into a reference cell 3a. The light from the light source 8 is divided into two halves by a half mirror 18 and the halved beams of light are caused to impinge upon the sample gases in the cells 3, 3a. The beams of scattered light emitted from the respective cells 3, 3a are received by the photoelectric amplifiers 4, 4a, converted into electric signals, and forwarded to a differential amplifier 14 to find the difference between the amount of light received from the measuring cell 3 and the amount of light received from the reference cell 3a. As a result, the accurate concentration of the specific gas for detection in the sample gas is displayed in the indicator 15.

As is evident from the foregoing description, the gas concentration measuring apparatus of the present invention effects the measurement of the concentration of the specific gas for detection contained in a sample gas by irradiating the sample gas with the ultraviolet light in the presence of oxygen thereby converting the specific gas into fine oxide particles and then measuring the intensity of scattered light caused by the fine oxide particles. Thus, the measuring apparatus is extremely simple in construction. When a semiconductor laser is adopted as the source for scattered light, the apparatus can be further reduced in size and the determination of the gas concentration can be performed easily and accurately. Further, the reaction velocity is heightened and the sensitivity is increased by enlarging the amount of the ultraviolet light used for the photochemical reaction. By proper selection of the wavelength of the ultraviolet light to be used for the irradiation of the sample gas, the formation of fine oxide particles of a specific gas can be attained in a plurality of species of gas. The gas concentration measuring apparatus of the present invention, therefore, is capable of detecting and measuring the specific gas contained in a minute amount in the waste gas emanating from the system for the manufacture of semiconductors or in the atmospheric air by using the gas directly as a sample gas instead of causing the gas to be passed through a complicated process of separation. Thus, it can be used advantageously as an automatic analyzer of high sensitivity.

Now, the present invention will be described more specifically below with reference to Examples.

EXAMPLE 1

A photochemical reaction chamber was prepared by disposing a 4.9-W mecury lamp as a source for ultraviolet light in a housing and providing windings of a quartz tube 1.5 mm in inside diameter around the external boundary of the lamp. The quartz tube had an overall length of about 600 mm. A brass tube 100 mm in length and 4 mm in inside diameter having the inner wall surface thereof coated with a black paint was used as a pipe in a measuring cell for scattered light. This measuring cell was provided at the portion thereof opposed to an electrophotographic amplifying tube with a window made of quartz glass. As a source for light used for irradiating a sample gas flowing through this brass tube, a 2-mW He-Ne laser (632.8 nm in wavelength) was used. The luminous flux from the laser was concentrated by the use of 50 mm and 100 mm focal-length lenses and a pinhole, so that the concentrated luminous flux would enter the tube through one end thereof. A photoelectric amplifier, type R-955, made by Photonics Co., Ltd. at Hamamatsu, Japan was used for the detection of scattered light emitted from the sample gas. Sample gases of varying phosphine concentrations ranging from 5 ppmV to 60 ppmV were prepared by mixing standard gas of 100 ppmV phosphine concentration with oxygen gas by the use of a mass flow controller. These sample gases were passed successively at a flow rate of 20 ml/min to the quartz tube in the photochemical reaction chamber of the apparatus constructed as described above, irradiated with ultraviolet light, and then led to the measuring cell to be irradiated with the laser beam to obtain data on the relation among the phosphine concentration of the gas for measurement, the intensity of scattered light, and the concentration of conglomerated particles in the gas. During the course of the measurement, the interior of the photochemical reaction chamber was kept swept with nitrogen gas.

The results of the measurement were as shown in FIG. 6. In the graph of FIG. 6, the open symbols indicate the values of the intensity of scattered light and the filled symbols the values of concentration of the phosphoric acid produced.

It is noted from the graph that the intensity of scattered light is proportional to the concentration of the phosphoric acid produced.

The fine oxide particles formed in the sample gas using oxygen gas as the carrier gas were tested for size and size distribution by a particle counter made by Dan Science Co. of Japan. The results were as shown in Table 1.

TABLE 1

| Conc. of $PH_3$ | Particle size ($\mu$m) | | |
|---|---|---|---|
| (ppmV) | 0.3–0.4 | 0.4–0.5 | 0.5–0.6 |
| 30 | 98.8(%) | 1.1(%) | 0.07(%) |
| 40 | 95.1 | 4.9 | 0.04 |

TABLE 1-continued

| Conc. of PH$_3$ | Particle size (μm) | | |
| --- | --- | --- | --- |
| (ppmV) | 0.3–0.4 | 0.4–0.5 | 0.5–0.6 |
| 50 | 83.5 | 16.0 | 0.5 |
| 60 | 65.3 | 31.8 | 2.9 |

A review of the data of this table coupled with those of the graph of FIG. 6 reveals that the size of the oxide particles formed in the gas increases in proportion as the concentration of phosphine increases (60%).

EXAMPLE 2

Sample gases independently containing 50 ppmV of phosphine and 40 ppmV of arsine and both using a mixed gas consisting of oxygen and helium in a ratio of 1:1 were pepared and were treated by the same apparatus as used in Example 1 to determine the relation between the flow rate of the gas and the intensity of the signal.

The results were as shown graphically in FIG. 7. In the graph, the curve "P" represents the data obtained in an experiment using the phosphine-containing gas as the sample gas and the curve "As" the data in an experiment using the arsine-containing gas as the sample gas. In the case of the phosphine gas, the peak intensity of the signal appeared when the flow rate was 10 ml/min. The signal intensity fell when the flow rate was further lowered possibly because the fine oxide particles once formed adhered to the inner wall surface of the quartz tube when they collided against the inner wall surface. In the case of arsine, the maximum intensity appeared where the flow rate was in the neighborhood of 5 ml/min. The optimum flow rate was smaller in this case than in the case of phosphine possibly because the speed of the photooxidation reaction and that of the conglomeration of fine oxide particles were lower in the case of arsine.

Then, sample gases containing phosphine and arsine separately in gradually decreasing concentrations were passed at decreasing flow rates through the apparatus to determine the detectable limits. Consequently, the limits were found to be 2 ppm for phosphine gas and 5 ppm for arsine gas.

EXAMPLE 3

Sample gases independently containing 50 ppmV of phosphine, arsine and stibine and all using oxygen as a carrier gas were prepared, and were passed to the same apparatus as used in Example 1 while varying the flow rate of the sample gases, irradiated with ultraviolet light, and measured with respect to the relation between the flow rate of the sample gases and the intensity of the signal obtained. The results were as shown graphically in FIG. 8. In the graph, the curve "P" represents the data obtained in an experiment using the phosphine-containing gas as the sample gas, the curve "As" the data in an experiment using the arsine-containing gas as the sample gas, and the curve "Sb" the data in an experiment using the stibine-containing gas as the sample gas.

EXAMPLE 4

Oxygen was supplied to the photochemical reaction chamber used in Example 1 at a flow rate of 6 ml/min controlled by a mass flow controller and, by actuating a six-way valve to change the flow passage of the oxygen, the oxygen was passed into a gas sampler having an inner volume of 1 ml and filled with a sample gas to expel the sample gas from the gas sampler and guide the expelled sample gas to the reaction chamber. Therefore, the sample gas was led to the reaction chamber as interposed between the oxygen supplied to the reaction chamber and the oxygen passed into the gas sampler. These gases were irradiated with ultraviolet light within the reaction chamber and the minimum content of the sample gas in the gases was detected. The results were as shown in Table 2 below.

TABLE 2

| Sample Gas | Minimum Content (ng) |
| --- | --- |
| PH$_3$ | 0.4 |
| AsH$_3$ | 1.5 |
| CH$_3$AsH$_2$ | 1.0 |
| SbH$_3$ | 2.0 |
| BiH$_3$ | 70 |
| SeH$_2$ | 3.0 |
| GeH$_4$ | 50 |
| SnH$_4$ | 2.0 |
| H$_2$S | 3.0 |

EXAMPLE 5

Ten ml of a sample gas containing GeH$_4$, AsH$_3$, SnH$_4$ and SbH$_3$ was passed through a column 900 mm in length and 4 mm in inner diameter and charged in advance with Porapak Q at room temperature for preconcentration. When the temperature of the column rose to 70° C., oxygen was introduced into the column at a flow rate of 10 ml/min and then the temperature of the column was increased by 8° C. per minute. The sample gas discharged out of the column was passed to the apparatus used in Example 1 and was continuously irradiated with ultraviolet light. The components of the sample gas was measured by the scattered light. As a result, the gases containing GeH$_4$, AsH$_3$, SnH$_4$ and SbH$_3$ were successively discharged at an interval of about 2 minutes and the contents thereof were 500 ng, 15 ng, 20 ng and 20 ng, respectively.

What is claimed is:

1. A gas concentration measuring method comprising the steps of:
    irradiating a sample gas containing trace amounts of a gas subjected to detection and capable of photochemically forming light-scattering oxide particles, exposing said sample gas to a photochemical intensity level of ultraviolet light in the presence of oxygen in a concentration of 20 to 100 percent at a temperature in the range of from normal room temperature to 60 degrees Centigrade, thereby forming fine oxide particles of the gas subjected to detection,
    irradiating the sample gas having the fine oxide particles contained therein with light, and
    detecting scattered light emitted by the fine oxide particles.

2. A gas concentration measuring method according to claim 1, wherein the gas subjected to measurement is at least one member selected from the group consisting of PH$_3$, AsH$_3$, CH$_3$AsH$_2$, SbH$_3$, BiH$_3$, SeH$_2$, GeH$_4$ and H$_2$S.

* * * * *